(12) United States Patent
Hendel et al.

(10) Patent No.: US 9,662,406 B2
(45) Date of Patent: *May 30, 2017

(54) UNIT DOSAGE OF APADENOSON

(71) Applicant: University of Virginia Patent Foundation, Charlottesville, VA (US)

(72) Inventors: Robert Hendel, Coconut Grove, FL (US); William B. Stilley, Charlottesville, VA (US); Shannon P. Williams, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,235

(22) Filed: Jun. 13, 2016

(65) Prior Publication Data

US 2017/0007722 A1    Jan. 12, 2017

Related U.S. Application Data

(60) Continuation of application No. 14/103,130, filed on Dec. 11, 2013, now Pat. No. 9,415,058, which is a division of application No. 13/544,364, filed on Jul. 9, 2012, which is a continuation of application No. 12/496,949, filed on Jul. 2, 2009, now abandoned.

(60) Provisional application No. 61/078,169, filed on Jul. 3, 2008, provisional application No. 61/155,937, filed on Feb. 27, 2009.

(51) Int. Cl.

| A61K 31/7076 | (2006.01) |
|---|---|
| A61K 49/00 | (2006.01) |
| A61K 9/00 | (2006.01) |
| A61K 31/519 | (2006.01) |
| A61K 47/02 | (2006.01) |
| A61K 47/12 | (2006.01) |
| A61K 47/40 | (2006.01) |

(52) U.S. Cl.
CPC ........ *A61K 49/0004* (2013.01); *A61K 9/0019* (2013.01); *A61K 31/519* (2013.01); *A61K 31/7076* (2013.01); *A61K 47/02* (2013.01); *A61K 47/12* (2013.01); *A61K 47/40* (2013.01)

(58) Field of Classification Search
None
See application file for complete search history.

(56) References Cited

U.S. PATENT DOCUMENTS

| 6,322,771 | B1 | 11/2001 | Linden et al. |
|---|---|---|---|
| 9,415,058 | B2 | 8/2016 | Hendel et al. |
| 2003/0162742 | A1 | 8/2003 | Linden et al. |
| 2004/0248776 | A1 | 12/2004 | Wisniewski et al. |
| 2005/0182018 | A1 | 8/2005 | Linden et al. |
| 2007/0020797 | A1 | 1/2007 | Pellizzer et al. |
| 2007/0207979 | A1 | 9/2007 | Podhajsky et al. |
| 2010/0003193 | A1 | 1/2010 | Hendel et al. |
| 2013/0017153 | A1 | 1/2013 | Hendel et al. |
| 2014/0100185 | A1 | 4/2014 | Hendel et al. |

FOREIGN PATENT DOCUMENTS

| AU | 2009266317 B2 | 12/2013 |
|---|---|---|
| CL | 40.063 | 9/2012 |
| CN | 102119023 B | 4/2014 |
| EP | 0413528 A1 | 2/1991 |
| EP | 2306971 A1 | 4/2011 |
| HK | 1156250 | 6/2012 |
| JP | 8508711 A | 9/1996 |
| JP | 2002536300 A | 10/2002 |
| JP | 2003502433 A | 1/2003 |
| JP | 2005508933 A | 4/2005 |
| JP | 2006515829 A | 6/2006 |
| JP | 2007536241 A | 12/2007 |
| JP | 2008508360 A | 3/2008 |
| JP | 2011526894 A | 10/2011 |
| JP | 2013177622 A | 9/2013 |
| KR | 1020110028531 A | 3/2011 |
| KR | 1020140021726 A | 2/2014 |
| WO | WO-9416733 | 8/1994 |
| WO | WO-0044763 A2 | 8/2000 |
| WO | WO-0078774 A2 | 12/2000 |
| WO | WO-03029264 A2 | 4/2003 |
| WO | WO-03086408 A1 | 10/2003 |
| WO | WO-2005107463 A1 | 11/2005 |
| WO | WO-2006015357 A2 | 2/2006 |
| WO | WO-2009011893 A2 | 1/2009 |
| WO | WO-2010002473 A1 | 1/2010 |

OTHER PUBLICATIONS

Kern, Morton J, "Effects of Apadenoson, a Selective Adenosine A2a Receptor Agonist for Myocardial Perfusion Imaging, on Coronary Blood Flow Velocity in Conscious Patients", American Heart Association, Inc. Circulation, 2006 114, 11_582,Abstract 2780, (2006), 1 pg).*

"U.S. Appl. No. 12/496,949, Non Final Office Action mailed Dec. 30, 2011", 18 pgs.

"U.S. Appl. No. 12/496,949, Preliminary Amendment mailed Jan. 17, 2011", 5 pgs.

"U.S. Appl. No. 12/496,949, Response filed Aug. 29, 2011 to Restriction Requirement mailed Jul. 27, 2011", 7 pgs.

"U.S. Appl. No. 12/496,949, Restriction Requirement mailed Jul. 27, 2011", 9 pgs.

"U.S. Appl. No. 13/544,364 Pre-Appeal Brief Filed Apr. 11, 2016", 5 pgs.

"U.S. Appl. No. 13/544,364, Final Office Action mailed Nov. 9, 2015", 13 pgs.

"U.S. Appl. No. 13/544,364, Final Office Action mailed Dec. 17, 2013", 11 pgs.

(Continued)

*Primary Examiner* — David J Blanchard
*Assistant Examiner* — Daniel F Coughlin
(74) *Attorney, Agent, or Firm* — Schwegman Lundberg & Woessner P.A.

(57) ABSTRACT

The present invention provides a unit dosage of Apadenoson, a pharmacological stress agent, and use of the same as a pharmacologic agent for myocardial perfusion imaging.

19 Claims, 2 Drawing Sheets

(56) References Cited

OTHER PUBLICATIONS

"U.S. Appl. No. 13/544,364, Non Final Office Action mailed Jan. 18, 2013", 17 pgs.
"U.S. Appl. No. 13/544,364, Non Final Office Action mailed Jan. 23, 2015", 14 pgs.
"U.S. Appl. No. 13/544,364, Response filed Jun. 17, 2014 to Final Office Action mailed Dec. 17, 2013", 7 pgs.
"U.S. Appl. No. 13/544,364, Response filed Jul. 18, 2013 to Non Final Office Action mailed Jan. 18, 2013", 14 pgs.
"U.S. Appl. No. 13/544,364, Response filed Jul. 23, 2015 to Non Final Office Action mailed Jan. 23, 2015", 8 pgs.
"U.S. Appl. No. 13/544,364, Response filed Dec. 26, 2012 to Restriction Requirement mailed Nov. 26, 2012", 7 pgs.
"U.S. Appl. No. 13/544,364, Restriction Requirement mailed Nov. 26, 2012", 8 pgs.
"U.S. Appl. No. 14/103,130, Amendment Under 37 C.F.R. § 1.312 filed Mar. 7, 2016", 5 pgs.
"U.S. Appl. No. 14/103,130, Notice of Allowability mailed Jul. 22, 2016", 4 pgs.
"U.S. Appl. No. 14/103,130, Notice of Allowance mailed Mar. 1, 2016", 9 pgs.
"U.S. Appl. No. 14/103,130, PTO Response to Rule 312 Communication mailed Apr. 7, 2016", 2 pgs.
"U.S. Appl. No. 14/103,130, PTO Response to Rule 312 Communication mailed May 10, 2016", 2 pgs.
"U.S. Appl. No. 14/103,130, Response filed Aug. 14, 2015 to Restriction Requirement mailed Mar. 5, 2015", 6 pgs.
"U.S. Appl. No. 14/103,130, Restriction Requirement mailed Mar. 5, 2015", 9 pgs.
"U.S. Appl. No. 14/103,130, Supplemental Amendment Filed Nov. 6, 2015", 7 pgs.
"Australian Application Serial No. 2009266317, Examiner's First Report mailed Feb. 17, 2012", 2 pgs.
"Australian Application Serial No. 2009266317, Office Action mailed Jun. 14, 2013", 3 pgs.
"Australian Application Serial No. 2009266317, Office Action mailed Nov. 15, 2013", 3 pgs.
"Australian Application Serial No. 2009266317, Response filed May 17, 2013 to Office Action mailed Feb. 17, 2012", 16 pgs.
"Australian Application Serial No. 2009266317, Response filed Nov. 8, 2013 to Office Action mailed Jun. 14, 2013", 27 pgs.
"Australian Application Serial No. 2009266317, Response filed Nov. 18, 2013 to Office Action mailed Nov. 15, 2013", 6 pgs.
"Canadian Application Serial No. 2,729,819, Office Action mailed Jun. 27, 2012", 2 pgs.
"Canadian Application Serial No. 2,729,819, Response filed Dec. 21, 2012 to Office Action mailed Jun. 27, 2012", 2 pgs.
"Canadian Application Serial No. 2,729,819, Voluntary Amendment mailed Dec. 18, 2013", 5 pgs.
"Chilean Application Serial No. 1617-10, Office Action mailed Feb. 15, 2011", 1 pg.
"Chilean Application Serial No. 1617-10, Office Action mailed Nov. 27, 2012", 6 pgs.
"Chilean Application Serial No. 1617-10, Response filed May 12, 2011", 19 pgs.
"Chilean Application Serial No. 1617-2010, Office Action mailed Apr. 6, 2016", 1 pg.
"Chilean Application Serial No. 1617-2010, Office Action mailed Jul. 15, 2014", 6 pgs.
"Chilean Application Serial No. 1617-2010, Response filed Feb. 14, 2013 to Office Action mailed Nov. 27, 2012", 5 pgs.
"Chilean Application Serial No. 1617-2010, Response filed Sep. 8, 2014", 8 pgs.
"Chinese Application Seria No. 200980131395.6, Office Action mailed May 4, 2012", W/English Translation, 11 pgs.
"Chinese Application Serial No. 200980131395.6, Office Action mailed Mar. 27, 2013", w/English Translation, 14 pgs.
"Chinese Application Serial No. 200980131395.6, Response filed Aug. 12, 2013 to Office Action mailed Mar. 27, 2013", w/English Claims, 10 pgs.
"Chinese Application Serial No. 200980131395.6, Response filed Nov. 19, 2012 to Office Action mailed May 4, 2012", With English Claims, 9 pgs.
"Dosage form", Wikipedia, [Online]. Retrieved from Internet: <http://en.wikipedia.org/wiki/Dosage_form>, (Apr. 18, 2013), 1-4.
"Eurasian Application Serial No. 201100132, Office Action mailed Jan. 29, 2013", w/English Translation, 3 pgs.
"Eurasian Application Serial No. 201100132, Office Action mailed Mar. 24, 2014", w/English Translation, 9 pgs.
"Eurasian Application Serial No. 201100132, Office Action mailed Jun. 3, 2014", w/English Translation, 5 pgs.
"Eurasian Application Serial No. 201100132, Office Action mailed Aug. 31, 2012", w/English Translation, 3 pgs.
"Eurasian Application Serial No. 201100132, Office Action mailed Oct. 24, 2013", w/English Translation, 2 pgs.
"Eurasian Application Serial No. 201100132, Response filed Jan. 29, 2013 to Office Action mailed Aug. 31, 2012", w/English Claims, 5 pgs.
"Eurasian Application Serial No. 201100132, Response filed Mar. 21, 2014 to Office Action mailed Oct. 24, 2013", w/English Claims, 10 pgs.
"Eurasian Application Serial No. 201100132, Response filed Aug. 20, 2013 to Office Action mailed Feb. 27, 2013", w/English Claims, 5 pgs.
"Eurasian Application Serial No. 201100132, Response filed Oct. 3, 2014", w/English Claims, 24 pgs.
"European Application Serial No. 09773926.2, Office Action mailed Feb. 14, 2011", 2 pgs.
"European Application Serial No. 09773926.2, Office Action mailed Jul. 17, 2013", 8 pgs.
"European Application Serial No. 09773926.2, Response filed Jan. 21, 2014 to Office Action mailed Jul. 17, 2013", 7 pgs.
"European Application Serial No. 09773926.2, Response filed Mar. 14, 2011 to Office Action mailed Feb. 14, 2011", 5 pgs.
"International Application Serial No. PCT/US2009/003939, International Preliminary Report on Patentability mailed Jul. 3, 2008", 6 pgs.
"International Application Serial No. PCT/US2009/003939, International Search Report mailed Oct. 28, 2009", 4 pgs.
"International Application Serial No. PCT/US2009/003939, Written Opinion mailed Oct. 28, 2009", 9 pgs.
"Israel Application Serial No. 210428, Office Action mailed Jul. 2, 2015", in English, 2 pgs.
"Israel Application Serial No. 210428, Response filed Oct. 29, 2015 to Office Action mailed Jul. 2, 2015", w/ English Claims, 8 pgs.
"Israeli Application Serial No. 210428, Office Action mailed Feb. 16, 2014", 3 pgs.
"Israeli Application Serial No. 210428, Office Action mailed Nov. 13, 2012", 2 pgs.
"Japanese Application Serial No. 2011-516343, Appeal Decision mailed Nov. 24, 2015", 12 pgs.
"Japanese Application Serial No. 2011-516343, Final Office Action mailed Apr. 30, 2013", w/ English Claims, 3 pgs.
"Japanese Application Serial No. 2011-516343, Office Action mailed Mar. 18, 2015", w/ English Translation, 14 pgs.
"Japanese Application Serial No. 2011-516343, Office Action mailed Jul. 11, 2014", not in English, 3 pgs.
"Japanese Application Serial No. 2011-516343, Office Action mailed Dec. 19, 2012", w/ English Claims, 7 pgs.
"Japanese Application Serial No. 2011-516343, Response filed Mar. 13, 2013 to Office Action mailed Dec. 19, 2012", With English Claims, 7 pgs.
"Japanese Application Serial No. 2011-516343, Response filed Aug. 29, 2013", w/English Claims, 74 pgs.
"Japanese Application Serial No. 2011-516343, Response filed Oct. 9, 2014", w/English Claims, 8 pgs.
"Japanese Application Serial No. 2011-516343, Response filed Sep. 18, 2015 to Office Action mailed Mar. 18, 2015", w/ English Claims, 10 pgs.
"Japanese Application Serial No. 2011-516343, Voluntary Amendment filed Jan. 20, 2011", w/ English Claims, 22 pgs.
"Japanese Application Serial No. 2013-177622, Examiners Decision of Final Refusal mailed Jan. 22, 2016", 3 pgs.

(56) References Cited

OTHER PUBLICATIONS

"Japanese Application Serial No. 2013-177622, Office Action mailed Jun. 17, 2015", 4 pgs.
"Japanese Application Serial No. 2013-177622, Office Action mailed Sep. 24, 2014", 2 pgs.
"Japanese Application Serial No. 2013-177622, Response filed Dec. 17, 2015 to Office Action mailed Jun. 17, 2015", 2 pgs.
"Korean Application Serial No. 10-2011-7002495, Appeal Brief filed Mar. 26, 2014", 13 pgs.
"Korean Application Serial No. 10-2011-7002495, Final Office Action mailed Jul. 24, 2013", 9 pgs.
"Korean Application Serial No. 10-2011-7002495, Final Office Action mailed Nov. 6, 2013", 8 pgs.
"Korean Application Serial No. 10-2011-7002495, Office Action mailed Jan. 3, 2013", 11 pgs.
"Korean Application Serial No. 10-2011-7002495, Response filed Mar. 4, 2013 to Office Action mailed Jan. 3, 2013", With English Claims, 22 pgs.
"Korean Application Serial No. 260030, Response filed Oct. 23, 2013 to Office Action mailed Jul. 24, 2013", 11 pgs.
"Malaysian Application Serial No. PI 2010006339, Office Action mailed Jan. 15, 2014", in English, 4 pgs.
"Malaysian Application Serial No. PI 2010006339, Office Action mailed Aug. 30, 2016", 2 pgs.
"Malaysian Application Serial No. PI 2010006339, Response filed Mar. 14, 2014 to Office Action mailed Jan. 15, 2014", English Translation, 7 pgs.
"Malaysian Application Serial No. PI 2010006339, Response filed Oct. 17, 2016 to Office Action mailed Aug. 30, 2016", 5 pgs.
"Malaysian Application Serial No. PI 2010006339, Voluntary Amendment mailed May 13, 2011", English Translation, 7 pgs.
"Mexican Application Serial No. MX/a/2011/000193, Office Action mailed Jun. 3, 2014", English Translation, 1 pg.
"Mexican Application Serial No. MX/a/2011/000193, Office Action mailed Sep. 24, 2013", 4 pgs.
"Mexican Application Serial No. Mx/a/2011/000193, Office Action mailed Oct. 28, 2014", not in English, 2 pgs.
"Mexican Application Serial No. MX/a/2011/000193, Response filed Jan. 27, 2014 to Office Action mailed Sep. 24, 2013", 9 pgs.
"Mexican Application Serial No. MX/a/2011/000193, Response filed Aug. 8, 2014 to Office Action mailed Jun. 3, 2014", w/English Claims, 13 pgs.
"New Zealand Application Serial No. 590489, First Examiner Report mailed May 30, 2011", 2 pgs.
"New Zealand Application Serial No. 590489, Office Action mailed Nov. 28, 2012", 1 pg.
"New Zealand Application Serial No. 590489, Response filed Nov. 21, 2012 to Office Action mailed May 30, 2011", 16 pgs.
"New Zealand Application Serial No. 590489, Response filed Dec. 5, 2012 to Office Action mailed Nov. 28, 2012", 8 pgs.
"Philippines Application Serial No. 1-2010-502960, Office Action mailed Jul. 23, 2014", 2 pgs.
"Philippines Application Serial No. 1-2010-502960, Response filed Sep. 23, 2014", 24 pgs.
"Singapore Application Serial No. 201009724-4, Office Action mailed Aug. 2, 2012", Written Opinion and Search Report, 15 pgs.
"Singapore Application Serial No. 201009724-4, Amendment filed Sep. 23, 2011", 6 pgs.
"Singapore Application Serial No. 201009724-4, Office Action mailed Jan. 24, 2014", 7 pgs.
"Singapore Application Serial No. 201009724-4, Office Action mailed May 17, 2013", 7 pgs.
"Singapore Application Serial No. 201009724-4, Response filed Oct. 17, 2013 to Office Action mailed May 17, 2013", 34 pgs.
"Singapore Application Serial No. 201009724-4, Response filed Dec. 28, 2012 to Office Action mailed Aug. 2, 2012", 4 pgs.
"Ukrainian Application Serial No. 2011 01125, Office Action mailed Apr. 23, 2013", 3 pgs.
"Ukrainian Application Serial No. 2011 01125, Office Action mailed Jul. 18, 2013", 2 pgs.
"Ukrainian Application Serial No. 2011 01125, Office Action mailed Jul. 30, 2014", 4 pgs.
"Ukrainian Application Serial No. 2011 01125, Office Action mailed Dec. 24, 2013", w/English Translation, 6 pgs.
"Ukrainian Application Serial No. 2011 01125, Response filed Jun. 18, 2013 to Office Action mailed Apr. 25, 2013", 5 pgs.
"Ukrainian Application Serial No. 2011 01125, Response filed Sep. 26, 2013 to Office Action mailed Jul. 18, 2013", 6 pgs.
"Vietnam Application Serial No. 1-2011-00184, Office Action mailed Feb. 18, 2016", 4 pgs.
"Vietnam Application Serial No. 1-2011-00184, Office Action mailed Jul. 7, 2011", 4 pgs.
"Vietnam Application Serial No. 1-2011-00184, Office Action mailed Jul. 18, 2013", 3 pgs.
"Vietnam Application Serial No. 1-2011-00184, Office Action mailed Dec. 18, 2014", w/ English Translation, 2 pgs.
"Vietnam Application Serial No. 1-2011-00184, Response filed Aug. 15, 2011 to Non Final Office Action dated Jul. 7, 2011", 9 pgs.
"Vietnam Application Serial No. 1-2011-00184, Response filed Nov. 18, 2013 to Office Action mailed Jul. 18, 2013", 5 pgs.
Brewster, M E, et al., "Parenteral safety and uses of 2-hydroxypropyl beta-cyclodextrin", Proceedings of the International Symposium Oncyclodextrins, (Mar. 28, 1990), 525-534.
Cerqueira, Manuel D, et al., "Advances in pharmacologic agents in imaging: new A2A receptor agonists", XP002550614 Database accession No. NLM16524538: Current Cardiology Reports, 8(2), (Mar. 2006), 119-122.
Cerqueira, Manuel D, et al., "The Future of Pharmacologic Stress: Selective A2A Adenosine Receptor Agnonists", American Journal of Cardiology, 94(suppl), (2004), 33D-42D.
Hendel, R. C., "Pharmacologic Stress: Evidence-Based/Pharmacologic Stress Tomorrow", 4th Annual Nuclear Cardiology and Cardiac CT, [online]. Retrieved from the Internet: <URL: http://www.acc.org/education/programs/brochures/pdfs/nuc-cardnew_07/thur%202pm%20Hendel%20pharm%202.pdf>, (2005), 27 pgs.
Hendel, R. C., et al., "Preliminary Experience with BMS068645, a Selective A2a Adenosine Agonist, for Pharmacologic Stress Myocardial Perfusion Imaging", American Heart Association, (Abstract Only), (2005), 1 pg.
Jain, D., "Advances in Pharmacological Stress Perfusion Imaging", Business Briefing: Future Directions in Imaging, (2006), 1-3.
Kern, M. J., "Effects of Apadenoson, a Selective Adenosine A2a Receptor Agonist for Myocardial Perfusion Imaging, on Coronary Blood Flow Velocity in Conscious Patients", Circulation, 114(II), [online]. Retrieved from the Internet: <URL: http://circ.ahajournals.org/cgi/content/meeting_abstract/114/18_MeetingAbstracts/II_582-a>, (2006), 3 pgs.
Kern, Morton J, "Effects of Apadenoson, a Selective Adenosine A2a Receptor Agonist for Myocardial Perfusion Imaging, on Coronary Blood Flow Velocity in Conscious Patients", American Heart Association, Inc. Circulation, 2006 114, II_582, Abstract 2780, (2006), 1 pg.
Miller, D. D., "Impact of Selective Adenosine A2A Receptor Agonists on Cardiac Imaging", Journal of the American College of Cardiology, 46(11), (2005), 2076-2078.
Rajewski, R, et al., "Pharmaceutical Applications of Cyclodextrins. 2. in Vito Drug Delivery", Journal of Pharmaceutical Sciences 85(11), (1996), 1142-1169.
Ruzin, "Buffer", Plant Microtechnique and Microscopy, available at<http://microscopy.berkeley.edu/Resources/instruction/buffers.html>; retrieved Dec. 3, 2011, (1999), 6 pgs.
Yang, Hong, et al., "Synthesis of [1,2-3H]ethylamine hydrochloride and [3H]-labeled apadenoson for a human ADME study,", J. Label Compd. Radiopharm. vol. 51, (Jan. 30, 2008), 113-117 pgs.

* cited by examiner

UNIT DOSAGE OF APADENOSON

CROSS-REFERENCE TO RELATED APPLICATIONS

The present application is a continuation of U.S. patent application Ser. No. 14/103,130, filed on Dec. 11, 2013, now U.S. Patent No. 9,415,058, issued 16 Aug. 2016, which is a divisional of U.S. patent application Ser. No. 13/544,364, filed on Jul. 9, 2012, now abandoned, which is a continuation of U.S. patent application Ser. No. 12/496,949, filed on Jul. 2, 2009, now abandoned, which claims the priority benefits of U.S. Provisional Applications No. 61/078,169, filed Jul. 3, 2008 and No. 61/155,937, filed Feb. 27 2009, which are expressly incorporated fully herein by reference.

FIELD OF THE INVENTION

The present invention relates to a unit dosage of Apadenoson, a pharmacological stress agent, and use of the same as a pharmacologic agent for myocardial perfusion imaging.

BACKGROUND OF THE INVENTION

Apadenoson, shown below, was first described as a pharmacologic stress agent

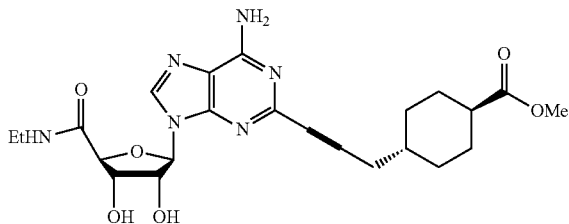

that can be used in clinical perfusion imaging techniques (e.g., for diagnosing and assessing the extent of coronary artery disease) in U.S. Pat. No. 6,322,771. This agent has since been taken into Phase I and II clinical trials. In 2005, Dr. Hendel et al reported to the American Heart Association on the preliminary results of 127 patient SPECT $Tc^{99m}$ sestamibi imaging studying comparing adenosine with Apadenoson using either 1 µg/kg or 2 µg/kg intravenous boluses of Apadenoson. The report concluded that Apadenoson was safe and well-tolerated and worthy of Phase III evaluation. In 2006, Dr. Kern et al reported to the American Heart Association the results of a Phase II study of Apadenoson, one goal of which was to determine an appropriate dose for Phase III clinical trials. Intravenous bolus dosages of 0.5, 1.0, 2.0, and 2.5 µg/kg were studied. For a patients, the average peak velocity for coronary blood flow was shown to increase with a corresponding increase in dosage from 0.5 to 2 µg/kg (see FIG. 1). In light of this data, it was believed that Apadenoson would need to be administered on a weight basis, not a unit dose basis.

There are inherent limitations and opportunities for operator error when parenterally administering a pharmaceutical agent on a weight basis. This type of dosing requires calculating the amount of agent to administer based on a patient's weight, administering the calculated amount from a larger dose, and disposing of any left over agent. Thus, it is desirable and beneficial for a pharmaceutical agent to be provided in a unit dose.

SUMMARY OF THE INVENTION

The present invention provides a novel unit dose of Apadenoson suitable for parenteral administration.

The present invention also provides a novel method of diagnosing myocardial dysfunction using a unit dose of Apadenoson as a pharmacologic stress agent.

These and other aspects of the present invention have been accomplished in view of the discovery that no dose response curve is seen when 1 µg/kg or 2 µg/kg of Apadenoson is administered.

DETAILED DESCRIPTION OF THE INVENTION

Figure 1:
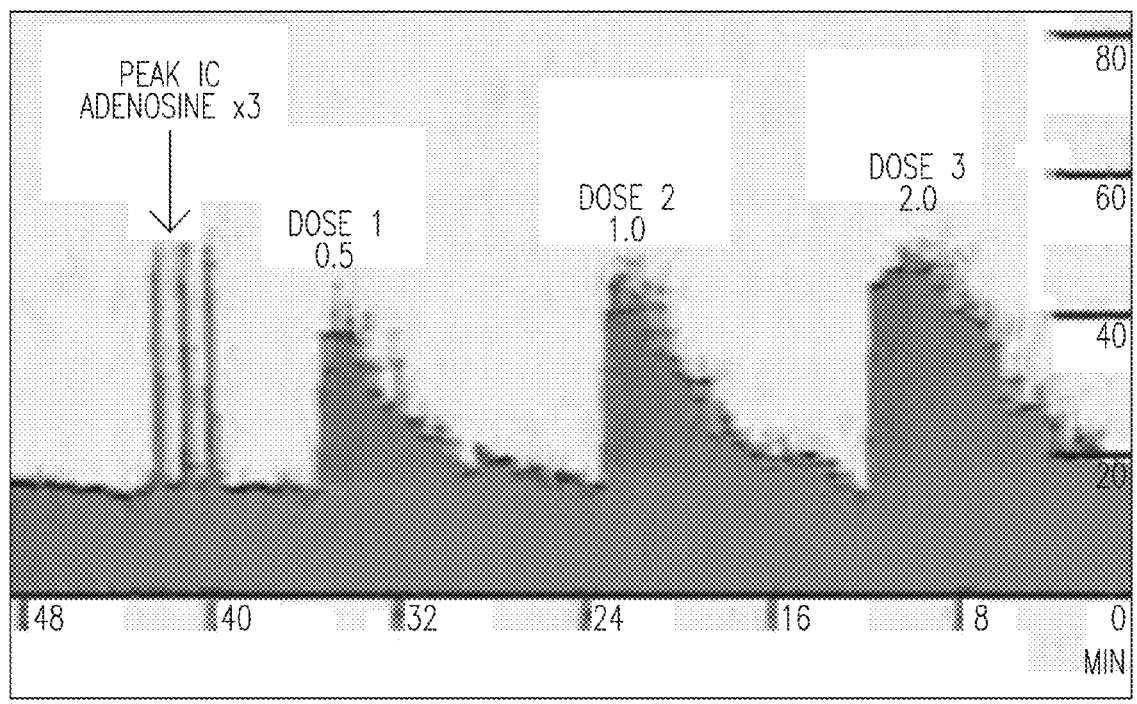
FIG. 1 shows the average peak flow wire velocity of one patient from a Phase II clinical trial study. In this Phase II study in 100 patients, conducted by Dr. Morton Kern, an independent investigator at UC Irvine, adenosine was administered by intracoronary injection, and coronary blood flow velocity was monitored with a flow wire. On the left, the three injections of adenosine increased blood flow velocity consistent with the well characterized pharmacology of adenosine. On the right, increasing bolus doses of Apadenoson, at doses shown to be safe, achieved peak flow equivalent to adenosine.
Figure 2:
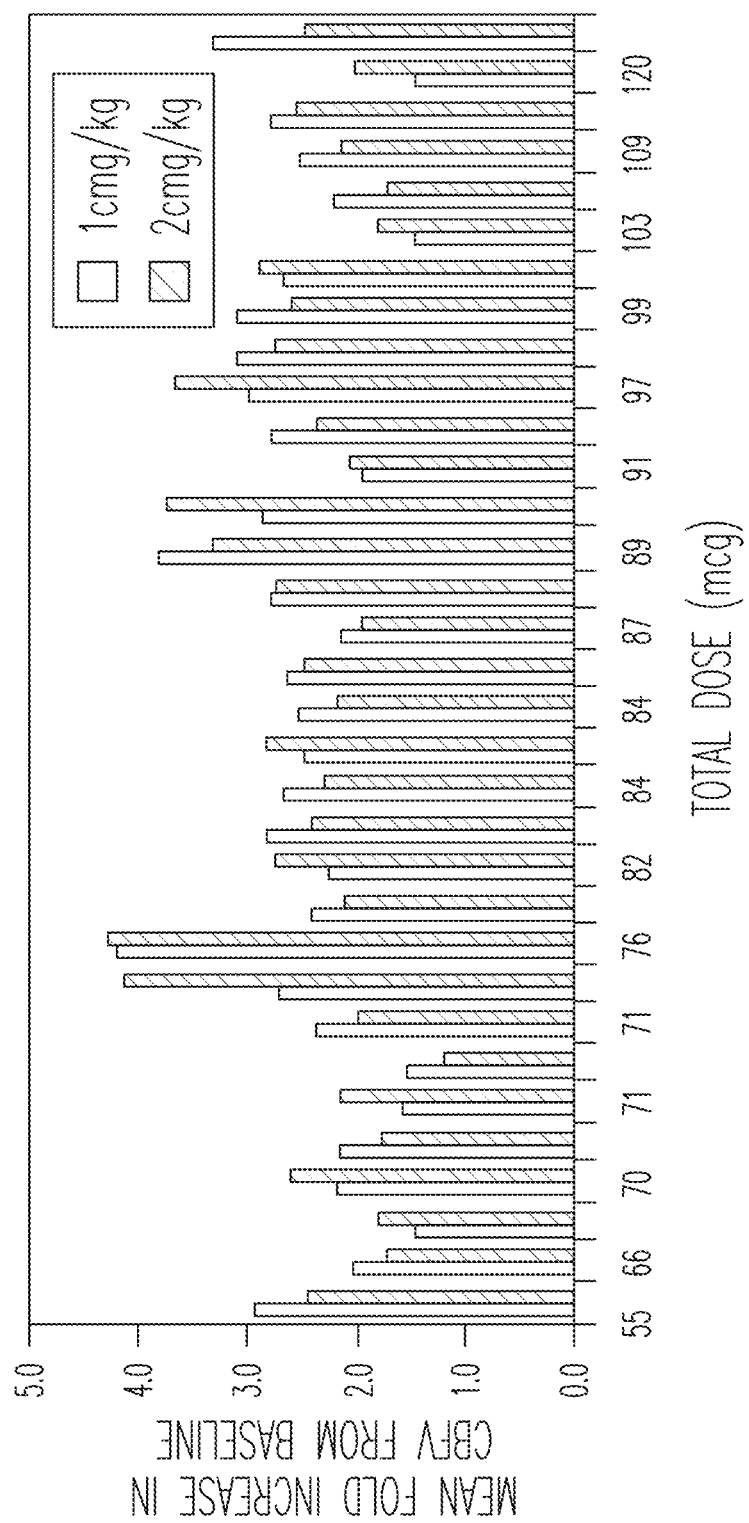
FIG. 2 shows the average peak flow wire velocity of 33 patients from the study described in FIG. 1.

The previously reported increase in coronary blood flow velocity (CBFV) corresponding to an increase in dose of Apadenoson from 0.5 to 2 µg/kg was based on the increase in CBFV in a limited number of patients (see FIG. 1). However, it has now been found that if one considers the entire sample of patients, as shown in FIG. 2, then at dose ≥1 µg/kg and in particular between 1 and 2.5 µg/kg no dose response is seen. In light of this, Applicant has surprisingly discovered that instead of the weight-based dosing predicted by the results reported in FIG. 1, Apadenson can actually be administered via a unit dose.

Thus, in an embodiment, the present invention provides a novel unit dose of Apadenoson, comprising: (a) Apadenoson and (b) a pharmaceutically acceptable carrier, wherein the unit dose is suitable for parenteral administration.

In another embodiment, the unit dose is suitable for intravenous administration.

In another embodiment, the amount of Apadenoson present in the unit dose is selected from 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, and 175 µg. Additional examples of the weight of Apadenoson present include (a) 100, 110, 120, 130, 140, and 150 µg; (b) 100 µg; and (c) 150 µg.

In another embodiment, the amount of Apadenoson present in the unit dose is in the range selected from 115, 116, 117, 118, 119, 120, 121, 122, 123, 124, to 125 µg. Additional examples of the weight of Apadenoson present include (a) 115, 120, and 125 µg and (b) 120 µg.

In another embodiment, the pharmaceutical carrier, comprises: a cyclodextrin. Examples of cyclodextrins include α-CD or derivatives thereof (e.g., α-hydroxypropyl-CD (HP-α-CD)), β-CD or derivatives thereof (e.g., β-hydroxypropyl-CD (HP-β-CD), methylated β-cyclodextrin, hydroxyethyl-β-cyclodextrin, and sulfobutylether β-CD), and γ-CD or derivatives thereof (e.g., γ-hydroxypropyl-CD (HP-γ-CD)).

Examples of the concentration of CD (e.g., hydroxypropyl-β-cyclodextrin) include being within the range selected from (a) about 0.1, 0.2, 0.3, 0.4, 0.5, 0.6, 0.7, 0.8, 0.9, 1, 2, 3, 4, 5, 6, 7, 8, 9, and 10% w/v; (b) about 0.5, 0.6., 0.7, 0.8, 0.9, 1, 2, 3, to 4% w/v; (c) about 1% w/v; and, (d) about 2% w/v of the final formulation.

In another embodiment, the pharmaceutical carrier, comprises: buffered saline. A useful buffer is a citrate buffer (e.g., sodium citrate). Citric acid can be useful to adjust the pH of the unit dose. As an example, the pharmaceutical carrier, comprises: buffered saline, comprising: saline, sodium citrate, and citric acid. One would recognize that citric acid may not be present in the final unit dose due to ionization.

In another embodiment, the pH of the unit dose is selected from 4.6, 4.7, 4.8, 4.9, to 5.0. Another example of the pH of the unit does is 4.8.

In another embodiment, the volume of the unit dose is selected from 1, 1.5, 2, 2.5, 3, 3.5, 4, 4.5, and 5 mL. Another example of the volume is from 2, 3, 4, to 5 mL.

In another embodiment, the unit dose, comprises:
(a) 100 µg Apadenoson;
(b) a pharmaceutically acceptable carrier, comprising:
  ($b_i$) 2% w/v HP-β-CD;
  ($b_{ii}$) sodium citrate buffer in an amount to buffer the unit dose to pH 4.8; and,
  ($b_{iii}$) saline in an amount to form a 1-5 mL unit dose.

In another embodiment, the unit dose, comprises:
(a) 100 µg Apadenoson;
(b) a pharmaceutically acceptable carrier, comprising:
  ($b_i$) 1% w/v HP-β-CD;
  ($b_{ii}$) sodium citrate buffer in an amount to buffer the unit dose to pH 4.8; and,
  ($b_{iii}$) saline in an amount to form a 1-5 mL unit dose.

In another embodiment, the unit dose, comprises:
(a) 150 µg Apadenoson;
(b) a pharmaceutically acceptable carrier, comprising:
  ($b_i$) 2% w/v HP-β-CD;
  ($b_{ii}$) sodium citrate buffer in an amount to buffer the unit dose to pH 4.8; and,
  ($b_{iii}$) saline in an amount to form a 1-5 mL unit dose.

In another embodiment, the unit dose, comprises:
(a) 150 µg Apadenoson;
(b) a pharmaceutically acceptable carrier, comprising:
  ($b_i$) 2% w/v HP-β-CD;
  ($b_{ii}$) sodium citrate buffer in an amount to buffer the unit dose to pH 4.8; and,
  ($b_{iii}$) saline in an amount to form a 1-5 mL unit dose.

The unit dose of the present invention can be filled into any useful container for storage, transportation, and usage. An example of a useful container is a syringe body.

In another embodiment, the present invention provides a novel method of diagnosing myocardial perfusion abnormalities in a mammal, comprising:
(a) parenterally administering to the mammal a unit dose of Apadenoson; and
(b) performing a technique on the mammal to detect the presence of coronary artery stenoses, assess the severity of coronary artery stenoses, or a combination thereof.

In another embodiment, the patient weighs at least 40 kg.

In another embodiment, the administration is intravenous administration.

In another embodiment, the technique is an imaging technique selected from: planar or single photon emission computed tomography (SPECT), gamma camera scintigraphy, positron emission tomography (PET), nuclear magnetic resonance (NMR) imaging, magnetic resonance imaging (MRI) imaging, perfusion contrast echocardiography, digital subtraction angiography (DSA), and ultrafast X-ray computed tomography (CINE CT).

In another embodiment, the present invention provides a prefilled syringe, comprising: a syringe and a unit dose of Apadenoson, comprising: (a) Apadenoson and (b) a pharmaceutically acceptable carrier, wherein the unit dose is suitable for parenteral administration. The syringe can be any known syringe useful for parenteral administration. For example, the syringe can comprise: a body and a plunger movably disposed within the body. The body can be cylindrical with a first open end to receive the plunger and a second end opposite the first, with the second end modified with an opening sufficient for the unit dose to pass through. The syringe can further comprise: a needle (e.g., an injection needle). The needle can be detachably connected to or permanently fixed to the body. A needle guard can also be present In another embodiment, the present invention provides a novel unit dose of Apadenoson for use in medical therapy.

In another embodiment, the present invention provides a novel use of a unit dose of Apadenoson for the manufacture of a medicament for use in diagnosing myocardial perfusion abnormalities in a mammal.

The Apadenoson unit dose of the present invention can be administered as a pharmacological stress agent and used in conjunction with any one of several noninvasive diagnostic procedures to measure aspects of myocardial, coronary, and/or ventricular perfusion. Aspects that can be measured include coronary artery stenoses, myocardial dysfunction (e.g., myocardial ischemia, coronary artery disease, ventricular dysfunction, and differences in blood flow through disease-free coronary vessels and/or stenotic coronary vessels), myocardial contractile dysfunction, the presence of regional wall motion abnormalities, the functional significance of stenotic coronary vessels, coronary artery disease, ischemic ventricular dysfunction, and vasodilatory capacity (reserve capacity) of coronary arteries in humans. Radiopharmaceuticals are typically used in diagnostic method methods. The radiopharmaceutical agent may comprise, for example, a radionuclide selected from the group consisting of thallium-201, technetium-99m, nitrogen-13, rubidium-82, iodine-123 and oxygen-15.

Any embodiment or feature of the present invention whether characterized as preferred or not characterized as preferred may be combined with any other aspect or feature of the invention, whether such other feature is characterized as preferred or not characterized as preferred.

Definitions

The examples provided in this application are non-inclusive unless otherwise stated. They include but are not limited to the recited groups.

Unit dose means the amount of a medication administered to a patient in a single dose. A unit dose is typically independent of the weight of the patient or may be associated with a specified weight range (e.g., ≥40kg).

The indefinite articles "a" and "an" mean "at least one" or "one or more" when used in this application, including the claims, unless specifically indicated otherwise.

Mammal and patient covers warm blooded mammals that are typically under medical care (e.g., humans and domesticated animals). Examples of mammals include (a) feline, canine, equine, and bovine and (b) human.

Parenteral includes intravenous, intramuscular, and subcutaneous routes.

Dosage and Formulation

Sterile injectable solutions are typically prepared by incorporating the active compound in the required amount in the appropriate solvent with various of the other ingredients enumerated above, as required, followed by filter sterilization (or some other form of sterilization). In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

All patents, patent applications, books and literature cited in the specification are hereby incorporated by reference in their entirety. In the case of any inconsistencies, the present disclosure, including any definitions therein will prevail.

Numerous modifications and variations of the present invention are possible in light of the above teachings. It is therefore to be understood that within the scope of the appended claims, the invention may be practiced otherwise that as specifically described herein.

What is claimed is:

1. A method of chemically inducing stress and diagnosing myocardial perfusion abnormalities in a mammal, comprising:
   (a) selecting a dose of Apadenoson between about 76-175 µg on a basis that is independent of the weight of the mammal to whom the dose will be administered;
   (b) administering to said mammal, via bolus, the dose of Apadenoson as a unit dose comprising Apadenson and a pharmaceutically acceptable carrier; and
   (c) performing a technique to detect the presence of coronary artery stenoses in the mammal, to assess the severity of coronary artery stenoses in the mammal, or a combination thereof, so as to diagnose myocardial perfusion abnormalities in said mammal.

2. The method of claim 1, wherein the unit dose further contains an effective amount of β-hydroxypropyl-cyclodextrin (HP-β-CD).

3. The method of claim 2, wherein the amount of HP-β-CD is about 0.1-10% w/v of the final formulation.

4. The method of claim 2, wherein the amount of HP-β-CD is 1% w/v.

5. The method of claim 1, wherein the dose of Apadenoson is 76 µg.

6. The method of claim 1, wherein the dose of Apadenoson is 110 µg.

7. The method of claim 1, wherein the dose of Apadenoson is 115 µg.

8. The method of claim 1, wherein the dose of Apadenoson is 120 µg.

9. The method of claim 1, wherein the dose of Apadenoson is 125 µg.

10. The method of claim 1, wherein the dose of Apadenoson is 130 µg.

11. The method of claim 1, wherein the dose of Apadenoson is 140 µg.

12. The method of claim 1, wherein the unit dose is 1 mL in volume.

13. The method of claim 1, wherein the unit dose is 2 mL in volume.

14. The method of claim 1, wherein the unit dose is 3 mL in volume.

15. The method of claim 1, wherein the unit dose is 4 mL in volume.

16. The method of claim 1, wherein the unit dose is 5 mL in volume.

17. The method of claim 1, wherein the dose of Apadenoson is selected on the basis of a single weight of Apadenoson being effective in previously tested mammals having a range of different weights.

18. The method of claim 1, wherein the unit dose further contains sodium citrate buffer.

19. The method of claim 18, wherein sodium citrate buffer is present in an amount to buffer the unit dose to pH selected from 4.6-5.0.

* * * * *